United States Patent [19]

Rasmussen

[11] Patent Number: 4,975,967
[45] Date of Patent: Dec. 4, 1990

[54] EARPLUG FOR NOISE PROTECTED COMMUNICATION BETWEEN THE USER OF THE EARPLUG AND SURROUNDINGS

[76] Inventor: Steen B. Rasmussen, Birkholmuei 1, DK-3540, Lynge, Denmark

[21] Appl. No.: 355,201

[22] Filed: May 22, 1989

[30] Foreign Application Priority Data

May 24, 1988 [DK] Denmark ............................ 2820/88

[51] Int. Cl.$^5$ ........................ H04R 25/02; H04R 1/10
[52] U.S. Cl. .................................. 381/187; 381/68.6; 181/135
[58] Field of Search ...................... 381/187, 183, 68.6; 181/130, 135; 128/867, 863, 864, 865, 866

[56] References Cited

U.S. PATENT DOCUMENTS

| Re. 29,487 | 12/1977 | Gardnen, Jr. ........................ 128/864 |
| 1,355,276 | 10/1920 | Schultz .................................. 128/864 |
| 2,246,737 | 6/1941 | Knudsen ............................... 128/865 |
| 2,427,664 | 9/1947 | Dunbar et al. ........................ 128/867 |
| 2,430,229 | 11/1947 | Kelsey .................................. 181/130 |
| 2,487,038 | 11/1949 | Baum .................................... 181/135 |
| 2,824,558 | 2/1958 | Michael et al. ....................... 181/135 |
| 2,888,921 | 6/1959 | Nielson et al. ....................... 128/865 |
| 3,209,082 | 9/1965 | McCarrell et al. ................. 381/68.6 |
| 3,890,474 | 6/1975 | Glicksberg .......................... 179/107 |
| 4,006,796 | 2/1977 | Coehorst ............................. 181/130 |
| 4,150,262 | 3/1979 | Ono ..................................... 381/68.6 |
| 4,442,917 | 4/1984 | Johnson .............................. 181/135 |
| 4,459,247 | 7/1984 | Rothemund ......................... 264/22 |
| 4,540,063 | 9/1985 | Ochi et al. ........................... 128/867 |

FOREIGN PATENT DOCUMENTS

| 969733 | 7/1958 | Fed. Rep. of Germany . |
| 1109737 | 6/1961 | Fed. Rep. of Germany . |
| WO88/03740 | 5/1988 | PCT Int'l Appl. . |

OTHER PUBLICATIONS

PCT/AU 83/00039-WIPO 83/03733 of Heyden Spike Co. Pty. Limited for Particle Entrainment Combustion, Oct. 27, 1983.

Primary Examiner—Jin F. Ng
Assistant Examiner—M. Nelson McGeary, III
Attorney, Agent, or Firm—Buchanan Ingersoll

[57] ABSTRACT

The earplug inserted in the auditory canal is so designed that its inside end facing the tympanic membrane makes close contact with the surrounding hard bone structure, and its external end at the aperture of the auditory canal makes close contact with the surrounding tissue. The earplug has a head for connection with a communication system. A central channel conveys sound to the tympanic membrane. The mid-section of the earplug is furnished with a circumferential recess for receiving sound waves from the user's own voice through the surrounding soft tissue: and channels convey these sound waves to a microphone built into the earplug head.

16 Claims, 1 Drawing Sheet

EARPLUG FOR NOISE PROTECTED COMMUNICATION BETWEEN THE USER OF THE EARPLUG AND SURROUNDINGS

FIELD OF THE INVENTION

The invention is directed toward an earplug for insertion in the auditory canal. Its function is to allow the user, by means of two separate acoustic systems, an earphone unit suitable for monitoring and a microphone unit, to engage in both simplex and duplex communication with another person in noisy surroundings.

DESCRIPTION OF THE PRIOR ART

There are numerous situations where someone must work in surroundings where there is intense noise, for example, work in an engine room or in the immediate vicinity of an aircraft, whose engines are a particularly loud source of noise.

Various devices have been used to enable such people to work despite the noise nuisance. For example an aircraft dispatcher can be furnished with ear protection and a hand-held radio transmitter/receiver. This solution is not very practical, partly because the radio set has to be hand-held (or worn on the body), and even more so because the actual microphone in the radio transmitter is also affected by the noise.

Various devices have therefore been developed which use an earplug which has a dual function: on the one hand to transmit sound waves to the user of the earplug through a channel of a type familiar from devices like hearing aids, and on the other to use the earphone as a high-impedance microphone that detects the sound signals which transmit the user's own voice through the oto-laryngeal system to the middle ear and out through the tympanic membrane to the earphone used as a microphone. As an example of this, reference may be made to PCT/AU83/0039-WIPO 83/03733.

The oto-laryngeal communications system described there is based on the use of an earplug with a built in microphone designed to detect the vibrations in the air column between the earplug in the auditory canal and the user's tympanic membrane and middle ear; it is specified in the PCT application cited that a microphone is used with "high impedance"—at least 1000 Ohms, preferably more than 2000 Ohms at 1 kHz.

The function of the system described is predicated on the assumption that the audio energy detected by the high-impedance microphone, and transmitted by means of bone conduction to the middle ear, gives the intended noise suppression in the cavity in front of the tympanic membrane as a result of the closure of the auditory canal by the earplug.

SUMMARY OF THE INVENTION

The earplug type we are concerned with here, however, differs in its function from the familiar technique in that the plug is designed, when inserted, to be in close contact with the wall of the auditory canal, both at the end facing the eardrum, where the plug is in contact with the surrounding bone through the auditory canal wall, and at the opposite end, where the auditory canal wall is in contact with the surrounding tissue. The earplug, at the mid-point between the two ends, has its outer surface at such a distance from the auditory canal wall that a cavity is formed at this point. The earplug is also able to transmit sounds signals both from its end surface at the aperture of the auditory canal to its end surface against the eardrum, and from the mid-point cavity to the end surface of the plug at the aperture of the auditory canal.

The invention is based on the realization that it is not particularly useful to base the functioning of the microphone on bone conduction between the middle ear and the tympanic membrane, and that much better results can be achieved by using sound conduction to the soft tissue surrounding the auditory canal, externally to the internal surface of the auditory canal at the bony part, and to a suitable point before it is transmitted further to the outer ear's hard bony structure around the auditory canal. The measurements made during the development of the present invention show that one achieves high-quality sound reproduction for the user's own voice and a suppression of up to 40 dB for outside noise.

The invention involves various solutions to the problem of obtaining close contact between the earplug and the auditory canal wall at the point where the structure of the wall changes from bone to soft tissue.

The earplug could, at least partially, consist of a molded core coated at the ends of the plug with a soft elastic material for contact with the auditory canal wall.

The earplug could also consist entirely of soft elastic material, for example of PVC foam material.

Since close contact is in fact only necessary at the inner and outer ends of the plug, the most suitable form for this coating of soft elastic material might be two PVC foam O rings sunk into the surface at each end of the plug.

To amplify the sound conduction effect from the soft tissue surrounding the auditory canal, the cavity mentioned above might best be formed as follows: on the surface of the earplug, and between its two ends, a circumferential recess could be made which, seen radially in relation to the axial direction of the earplug, is less deep than the extent of the recess in the longitudinal direction of the earplug. What one achieves with this is that the sound waves from the soft tissue are propagated in the cavity at right angles to the bottom surface of the cavity, so that the narrow channel from the bottom of the cavity—since the cross section of the channel is small compared with the area of the bottom of the cavity—transmits sound pressure waves of greater amplitude because of the amplification of the sound waves in the narrow channel.

While the cavity may be filled with air, it might also suitably be filled with a fluid. In this case a membrane could be laid in the bottom of the recess to contain the fluid in the recess.

For further protection of the signal coming from the recess against any residual noise that might penetrate, the invention specifications state that it might be expedient to use a sound-sensitive membrane of piezoelectric or piezo-resistive material, and that there could be at least two electrical circuits for transmission of electrical signals from the sound-pressure-sensitive membrane to the external end surface of the earplug.

An earplug of the type specified could also be distinctive inasmuch as the plug, at its external end surface, is furnished with, or designed for connection with, a head which will on the one hand transmit incoming signals to the tympanic membrane via the longitudinal channel, and on the other will receive speech signals from the cavity and transmit them to a unit, itself of a known type, for communication with the surroundings.

DRAWINGS

The invention is explained in more detail in the following, with references to the diagram, where FIG. 1 is a conventional cross section of a human ear with the earplug inserted as per the invention specifications;

DESCRIPTION BY REFERENCE TO DRAWINGS

Figure 1:
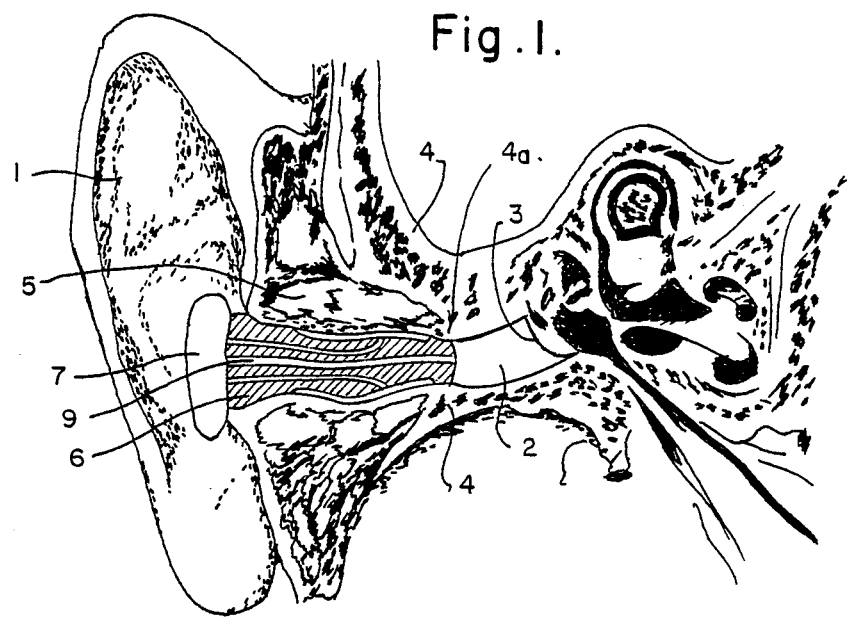

FIG. 1 is a quite conventional section through a human ear showing the auricle 1, the auditory canal 2, the tympanic membrane 3, the part of the bone structure of the head that surrounds part of the auditory canal 4, and the soft tissue surrounding the rest of the auditory canal 5 up to the auricle 1. The other parts of the inner ear need not be mentioned in detail here, as they are of no special significance for the understanding of the invention.

In the auditory canal 2 an earplug 6 has been inserted as per the specifications of the invention.

Figure 2:
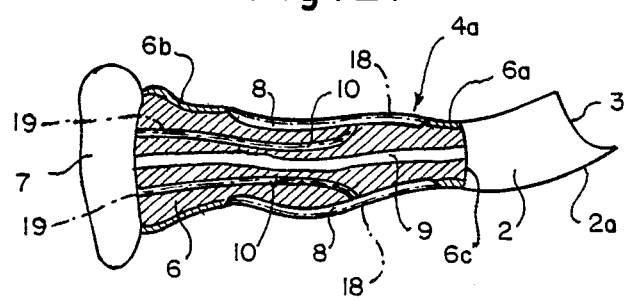
FIG. 2 shows the plug itself and optional membrane in the auditory canal.
Figure 3:
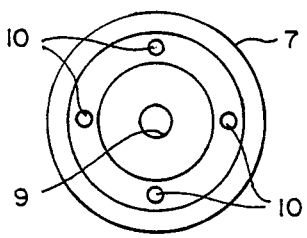
FIG. 3 shows an end view of the earplug seen from outside the ear.

FIG. 2 shows the earplug 6 inserted in the auditory canal. For the sake of clarity the rest of the ear has been omitted, and the figure only shows the plug 6, auditory canal 2 and tympanic membrane 3.

The earplug 6, oblong in shape, can in principle be shaped by conventional molding for the individual user, so that the shape is on the whole adapted to the shape of the user's auditory canal.

At the end of the earplug facing the tympanic membrane 3 the earplug is shaped so as to come into close or generally close contact with the part of the auditory canal wall 2a which is in direct contact with the transition 4a to the soft tissue 5. This inner end 6c should be at a suitable distance from the tympanic membrane 3. The zone of the earplug where there is close contact with the auditory canal wall 2a and the transitional section 4a between the bony part and the soft tissue has been shown with cross-hatching in FIG. 1, and can be seen more clearly, also with cross-hatching, in FIG. 2.

At the end facing away from the tympanic membrane 3 and just outside the aperture of the auditory canal, the earplug 6 is furnished with a head 7 which, as will be explained later in more detail, has the function of allowing the earplug to be connected with a signal transmitter/receiver.

Immediately behind the earplug head 7 the earplug 6 is shaped to have a collar 6b, as shown with cross-hatching, in close or generally close contact with the auditory canal wall 2a. A similar collar 6a is provided at the inner end of the earplug.

Between the two collars 6a and 6b of the earplug, there is a recess around the plug 6 so that when the plug is inserted in the ear, the portion of the body between the collars will not make close contact with the auditory canal wall 2a. When the earplug is in the ear canal the outer surface of this portion of the earplug will be at a certain distance from the auditory canal wall to form a cavity 8.

A longitudinal channel 9 runs through the whole earplug 6, stretching from the end surface 6c facing the tympanic membrane 3 to the earplug head 7.

From the bottom of the cavity 8 around the earplug, and mainly from the mid section of this cavity, there should run at least one, and preferably four, longitudinal channels 10, ending at the earplug head 7.

The earplug head 7 is designed for connection with a capsule not shown in the drawing, containing an audio signal transmitter placed outside the longitudinal channel 9 in the earplug, and a signal recorder linked with the cavity channel or channels 10.

The functioning of the earplug according to the specifications for the invention will now be explained in more detail.

An earplug inserted in the auditory canal makes close contact, as mentioned above, with the transitional section 4a between the bony part and the soft tissue, via the auditory canal wall 2a at the end portion 6a of the plug, and also makes close contact with the surrounding soft tissue 5 through the auditory canal wall 2a.

The audio signal transmitter, which for example could receive an electrical signal from a built-in radio receiver, propagates sound waves to the channel 9 which conveys these sound waves to the tympanic membrane 3. It is to be understood that these waves, on their way from the audio signal source at the earplug head 7 to the tympanic membrane, are propagated in planes extending at right angles to the channel axis 9 and thus also mainly at right angles to the axis of the auditory canal.

Because of the close contact between the ear canal wall and the collars 6a and 6b of the earplug 6 and because of the structure of the earplug itself, the bulk of any noise signal coming from a close, loud, noise source (for example, a jet engine), which would normally be an intense nuisance for the person in question, will be very substantially dampened.

The sound of the user's own voice is mainly transmitted through the soft tissue 5 outside the recess 8 in the earplug 6. The sound waves from such a sound will be propagated at right angles to the axis of the earplug channel 9; and the small cavity 8 which is less deep than its axial extent has an amplifying effect, so that the sound waves of the user's own voice will be further propagated in the cavity channels 10 to an audio receiver and transmitter built into the, capsule at the earplug head 7. The receiver and transmitter could, for example, be a microphone with an electric or electromagnetic signal transmitter, e.g. a radio transmitter.

We will now look in more detail at the way the earplug itself 6 can be shaped.

The earplug 6 can be produced by molding which will shape it to the individual ear form. The entire earplug or a core portion of the earplug body can be molded. For this molding process one could use standard plastic materials of the type used for ordinary hearing aids. To achieve close contact at the two collars 6a and 6b of the earplug 6, two circumferential grooves, one at each end of the plug, can be made by molding or a subsequent operation (hot-molding, milling, etc.), and then placing an O ring of soft, elastic or viscoelastic material in each groove. This material could for example be a slow recovery polymeric foam material of polyvinyl chloride, polyurethane or other material suitable for foam earplugs disclosed in U.S. Pat. No. Re. 29,487. This material can be greatly compressed and then expands and regains its normal shape in the course of a few seconds.

As another possibility, the bulk of the earplug could be designed in such a material; but to avoid closure of the channels 9 and 10 during compression, these channels could take the form of narrow tubes of non-compressible material so that auditory continuity is maintained through the channels.

The cavity 8 could be filled with air, but could also be filled with a layer of fluid with an appropriate membrane 18 shown in chain line in FIG. 2 to contain the fluid in the recess or at the outlets of the channel or channels 10.

It is also possible to detect the sound of the user's own voice directly at the bottom of the recess 8 through a membrane of piezo-electric or piezo-resistive material, so that the conversion of the acoustic to an electric signal would be placed directly at the recess. In this case the earplug would have at least two electrical conducting circuits 19 built in for transmission of the electrical signal to the earplug head 7 and a related signal transmitter (not shown) attached to the head.

While certain presently preferred embodiments of the present invention have been shown and described in the foregoing specification it is to be distinctly understood that the invention is not limited thereto but may be otherwise variously embodied with the scope of the following claims.

I claim:

1. An earplug intended for insertion in an ear canal and intended to allow the user of the earplug, by means of two separate acoustic systems consisting of an earphone unit suitable for monitoring and a microphone unit, to engage in both simplex and duplex communication with another person in noisy surroundings, comprising:
   (a) a body having a size and shape adapted to fit within the ear canal, an inner end, an outer head and a longitudinal channel passing through the body from the inner end to the outer head; and
   (b) a pair of collars surrounding the body which when the earplug is in the ear canal are sized and positioned to make contact with a wall of the ear canal and are spaced apart to create a cavity defined by the collars, a surface portion of the body between the collars and the ear canal wall; said body also having at least one cavity channel running from the outer head to the surface of the portion of the body between the collars.

2. An earplug as claimed in claim 1 wherein the body at least partially consists of a molded core and the collars are soft, elastic material for contact with the auditory canal wall.

3. The earplug of claim 2 wherein the soft, elastic material is a polyvinyl chloride foam.

4. An earplug as claimed in claim 1 wherein the earplug consists of soft, elastic material.

5. An earplug as claimed in claim 4 wherein said soft, elastic material is a polyvinyl chloride foam material.

6. An earplug as claimed in claim 1 wherein the collars are O-rings of soft, elastic material.

7. An earplug as claimed in claim 1 wherein at least one of the longitudinal channel and the cavity channel consist of narrow tubes of one of non-compressible material and mainly non-compressible material.

8. An earplug as claimed in claim 1 wherein the cavity is filled with air.

9. An earplug as claimed in claim 1 wherein the cavity is filled with a fluid.

10. An earplug as claimed in claim 1 also comprising a membrane attached to the portion of the body between the collars to contain a fluid within the cavity.

11. An earplug as claimed in claim 10 wherein the membrane is a sound-sensitive membrane made of one of piezo-electric and piezo-resistive material, and also comprising at least two electrical conducting circuits for transmission of an electrical signal from the sound-pressure-sensitive membrane to the outer end of the earplug.

12. The earplug as claimed in claim 1 wherein the outer head is sized and configured to receive at least one of a transmitter and a receiver.

13. The earplug as claimed in claim 1 wherein the collars are comprised of a slow recovery foam.

14. The earplug as claimed in claim 13 wherein the slow recovery foam is one of polyvinyl chloride and polyurethane.

15. The earplug as claimed in claim 1 wherein the body is comprised of a slow recovery foam.

16. The earplug as claimed in claim 15 wherein the slow recovery foam is one of polyvinyl chloride and polyurethane.

* * * * *